(12) United States Patent
Leclerc et al.

(10) Patent No.: US 7,128,914 B2
(45) Date of Patent: Oct. 31, 2006

(54) **PRODUCT CONTAINING AN EXTRACT OF RED ALGAE OF THE GENUS *PORPHYRA* AND METHODS FOR PROTECTING CELLS**

(75) Inventors: Christian Leclerc, Dun-sur Auron (FR); Francois Paul, Toulouse (FR)

(73) Assignee: Larena (FR)

( * ) Notice: Subject to any disclaimer, the term of this patent is extended or adjusted under 35 U.S.C. 154(b) by 74 days.

(21) Appl. No.: 10/844,675

(22) Filed: May 13, 2004

(65) Prior Publication Data

US 2004/0228875 A1    Nov. 18, 2004

Related U.S. Application Data

(63) Continuation of application No. PCT/FR02/03901, filed on Nov. 14, 2002.

(30) Foreign Application Priority Data

Nov. 14, 2001  (FR)  .................................. 0114731
Nov. 14, 2002  (FR)  .................................. 0214253

(51) Int. Cl.
*A61K 36/04* (2006.01)

(52) U.S. Cl. ................................................. 424/195.17

(58) Field of Classification Search ..................... None
See application file for complete search history.

(56) References Cited

FOREIGN PATENT DOCUMENTS

| | | | |
|---|---|---|---|
| FR | 2 655 268 A1 | 6/1991 | |
| FR | 2 803 200 A1 | 7/2001 | |
| FR | 2 803 201 A1 | 7/2001 | |
| JP | 06 263623 A | 9/1994 | |
| JP | 07 242523 A | 9/1995 | |
| JP | 09-067266 | * | 3/1997 |
| JP | 2000 212056 A | 8/2000 | |
| JP | 2002 06943 A | 3/2002 | |
| WO | WO 00/70968 A1 | 11/2000 | |

OTHER PUBLICATIONS

English abstract of JP 62-100294 (1987).*

* cited by examiner

*Primary Examiner*—Susan D. Coe
(74) *Attorney, Agent, or Firm*—DLA Piper

(57) ABSTRACT

A composition that induces synthesis of stress protective proteins during application of physical or physiological stresses, or physiopathological aggressions on cells including a water-alcohol extract of red algae, taurine and derivatives: about 1 to about 5%, floridoside and derivatives: about 10 to about 25%, one or more of carotenoids and PUFAs, one or more water-soluble vitamins, one or more free amino acids and derivatives, and one or more pigments; and a method of protecting skin against wrinkle formation including administering a therapeutically effective amount of a composition including a water-alcohol extract of red algae that induces synthesis of stress protective proteins during physical or physiological stresses, or physiopathological aggressions on skin cells.

6 Claims, 2 Drawing Sheets

PRODUCT CONTAINING AN EXTRACT OF RED ALGAE OF THE GENUS *PORPHYRA* AND METHODS FOR PROTECTING CELLS

RELATED APPLICATION

This is a continuation of International Application No. PCT/FRO2/03901, with an international filing date of Nov. 14, 2002 (WO 03/041679, published May 22, 2003), which is based on French Patent Application Nos. 01/14731, filed Nov. 14, 2001, and 02/14253, filed Nov. 11, 2002.

FIELD OF THE INVENTION

This invention pertains to the field of products based on algae extracts used as nutritional supplements and in cosmetic and dermatological applications for cell protection.

BACKGROUND

Red algae belonging to the genus *Porphyra* comprise multiple species including:

*Porphyra umbilicalis*, collected in Brittany; *Porphyra purpurea*, present in Brittany; *Porphyra tenera*, cultivated in Japan; *Porphyra yezoensis*, cultivated in Japan; and *Porphyra columbina*, collected in Australia.

The alimentary species of *Porphyra* are also called "nori." The species *Porphyra umbilicalis* forms a thin orbicular lanceolate lamella of purplish color which can reach 60 cm in length. The *Porphyra* species are the most widely consumed alimentary algae in the world. In France, the species *Porphyra umbilicalis* is approved for human alimentary consumption. The nutritional value of this algae stems from its richness in various compounds such as:

proteins, up to 45% of the dry matter, polyunsaturated fatty acids (PUFAs), such as EPA (eicosapentaenoic acid), up to 5% of the algae lipids, group B vitamins, vitamin B12 in particular, and vitamin A and the carotenoids.

The prior art contains descriptions of numerous properties of extracts of the algae *Porphyra* and the compounds that they contain such as, for example:

antioxidant properties of a methanol extract (80%) of *Porphyra tenera*; antioxidant properties of extracts in various polar and apolar solvents of *Porphyra yezoensis*, of the methanol extract, in particular; antioxidant properties of an extract made with methanol (50%) and acetone; the presence of high concentrations of taurine and its derivatives, soluble in water-alcohol medium, known for its elicitor properties of chaperone proteins (HSP); the presence of derivatives of soluble sugars in water-alcohol medium such as floridoside (alpha-D-galactopyranosyl-(1-2)-glycerol) and its isomers which play an essential role in the osmotic regulation of cell medium subjected to notable hydric stresses; and the presence of porphyran, polysaccharide of the gars family, not extracted because it is not soluble in water-alcohol solutions having an alcohol content greater than 70% which have immunostimulant and antitumor properties.

SUMMARY OF THE INVENTION

This invention relates to a composition that induces synthesis of stress protective proteins during application of physical or physiological stresses, or physiopathological aggressions on cells including a water-alcohol extract of red algae, taurine and derivatives: about 1 to about 5%, floridoside and derivatives: about 10 to about 25%, one or more of carotenoids and PUFAs, one or more water-soluble vitamins, one or more free amino acids and derivatives, and one or more pigments.

This invention also relates to a method of protecting skin against wrinkle formation including administering a therapeutically effective amount of a composition including a water-alcohol extract of red algae that induces synthesis of stress protective proteins during physical or physiological stresses, or physiopathological aggressions on skin cells.

This invention further relates to a method of inducing synthesis of stress protective proteins in skin including administering a therapeutically effective amount of a composition including a water-alcohol extract of red algae to a patient.

This invention still further relates to a method of protecting skin against thermal shock, UV radiation, infection and inflammation comprising administering a therapeutically effective amount of a composition comprising a water-alcohol extract of red algae that induces synthesis of stress protective proteins in the skin.

BRIEF DESCRIPTION OF THE DRAWINGS

Other advantages and characteristics of the invention will become apparent from the examples below concerning the activity of a water-alcohol extract of *Porphyra umbilicalis* on the response to thermal shock or UV radiation of cells in in-vitro culture. Reference will be made to these examples in the attached drawings in which.

DETAILED DESCRIPTION

Figure 1:
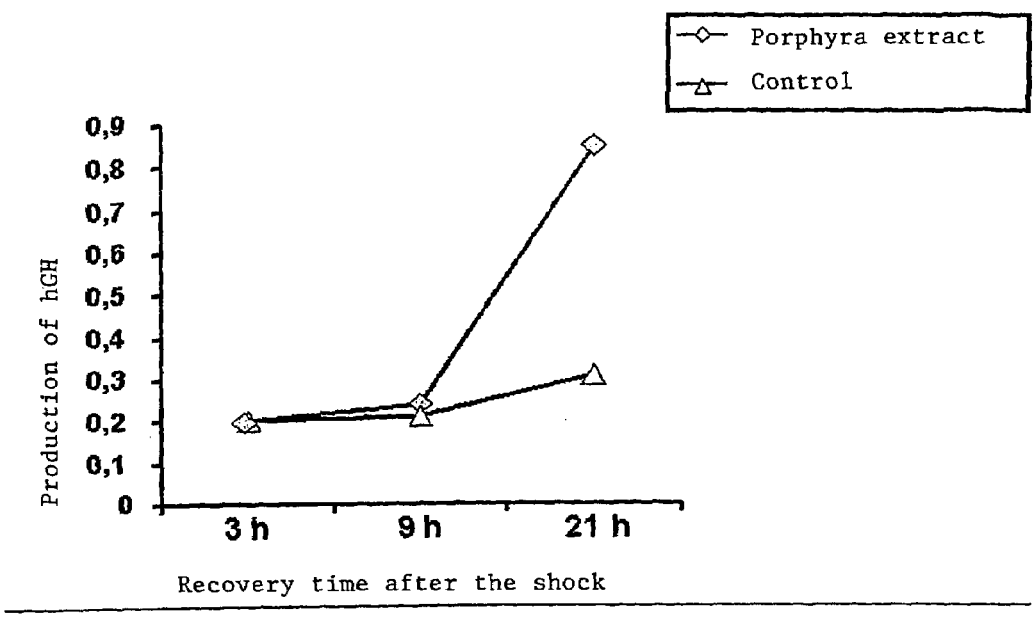
FIG. 1 shows the kinetics of the production of growth hormone (hGH) by CHO cells.

We have now demonstrated that a water-alcohol extract of the red algae *Porphyra umbilicalis* has the capacity to induce the synthesis of stress protective proteins during various physical stresses on cells. This unexpected capacity confers on these extracts a remarkable value for preparing active compositions for protecting cells from the stress caused by physiological or physical stresses such as a thermal shock or exposure to UV rays or even by physiopathological stresses notably infections and inflammations.

In fact, the synthesis of stress protective proteins described in response to treatments that accelerate the denaturation of proteins such as heat is a generalized defense mechanism developed by the cell to confront a very large diversity of aggressions. The stress protective proteins combine with proteins whose three-dimensional structure is altered by the fact of an aggression and participate in their elimination, their restoration or the stress proteins combine with proteins whose three-dimensional structure is not yet acquired (proteins in the process of biosynthesis) and participate in their maturation. The stress protective proteins thereby protect the cells by preserving the integrity of their components and thus their functionality.

The earlier induction of synthesis of stress protective proteins in response to an aggression and an enhanced synthesis of these proteins are thus the advantages for the cells conferring on them a more effective protection system.

The invention consequently provides a product that induces the synthesis of stress protective proteins during physical or physiological stresses or physiopathological aggressions on the cells. The product comprises or is constituted by a water-alcohol extract of red algae. Thus, the invention preferably pertains to an extract of red algae belonging to the genus *Porphyra*, and most preferably an extract of red algae of the species *Porphyra umbilicalis*.

The algae extract comprises the following compounds in proportions expressed by weight in relation to the total weight of the extract when they are analyzed quantitatively:
  taurine and derivatives: about 1 to about 5%,
  floridoside and derivatives: about 10 to about 25%,
  carotenoids and PUFAs (not quantitatively determined),
  water-soluble vitamins (not quantitatively determined),
  amino acids and derivatives (not quantitatively determined), and
  various pigments.

A product according to the invention comprises from about 1 to about 30% by weight of a water-alcohol extract of red algae in relation to the total weight of the product.
  The water-alcohol algae extract can be stabilized by:
  maltodextrins for subsequent use in powder form; a powder product according to the invention comprises from about 10 to about 30%, preferably from about 15 to about 25%, and most preferably on the order of about 20%, by weight of a water-alcohol extract of red algae in relation to the total weight of the product;
  glycerol for subsequent use in liquid form (except use for cosmetic compositions). A liquid product according to the invention comprises from about 10 to about 30%, preferably from about 15 to about 25%, and most preferably on the order of about 20%, by weight of a water-alcohol extract of red algae in relation to the total weight of the product; and
  addition of a preservative (PHENONIP® 0.5% w/w, for example) and a sterilizing filtration (0.2µ) for a use in cosmetic compositions; a liquid product according to the invention intended for use in cosmetic compositions comprises from about 1 to about 25, preferably from about 3 to about 20%, of a water-alcohol extract of red algae.

In powder form, the product can easily be incorporated in dry formulations of nutritional supplements and packaged in gel capsules, tablets, sachets and the like. The product is useful in liquid form for cosmetic preparations or packaging in soft capsules.

The invention pertains to a red algae extract or a product containing such an extract for a composition, notably alimentary or cosmetic, that induces the synthesis of stress proteins during various physical stresses on the cells. A composition according to the invention is most particularly useful for modulating the stress proteins HSP60, HSP27 and HSP70. We discovered that the composition of the invention demonstrated the capacities of the extract or of a product containing it to protect cells against thermal shock, UV radiation or any other physical or therapeutic shock. These properties make the compositions according to the invention of interest both in humans and animals.

Thus, the invention pertains to an extract of red algae or a product containing it for a composition, notably an alimentary or cosmetic composition, that protects cells against physiological stresses or physiopathological aggressions, in particular, infections and inflammations.

The invention also pertains to a red algae extract or a product containing such an extract for a composition, notably an alimentary or cosmetic composition, that protects cells against physical aggressions, thermal shock or UV radiation, in particular.

The thermal shocks may be hot thermal shocks and cold thermal shocks. Thus, the compositions according to the invention can also be used by individuals subjected to hostile environments such as the ocean or the mountains, and are thus especially suitable for divers and skiers, mountain climbers and high-altitude athletes.

With regard to exposure to UV radiation, the invention does not pertain to the use of the red algae extract or the product containing such an extract as a filter, but as a protective agent against the stress to which the cells are subjected during such an exposure.

The compositions of the invention intended to protect the cells against physical aggression, in particular a thermal shock or UV radiation, can be administered via the oral route or via the topical route.

The compositions according to the invention can constitute nutritional supplements for humans or feed supplements for animals providing per administration from about 10 to about 1000 mg, preferably from about 25 to about 250 mg, of a product containing the red algae extract. A composition according to the invention constituting a nutritional supplement or feed supplement can be made available in the form of gel capsules, soft capsules, tablets, sachets, syrup and the like.

The compositions according to the invention can also constitute cosmetic compositions, preferably dermatological compositions, applied topically to the skin. The compositions of the invention enable protection of the skin against physical aggressions and most particularly thermal shocks or UV radiation. The cosmetic compositions according to the invention are also useful as anti-aging compositions for improving the qualities and appearance of the skin.

The cosmetic compositions according to the invention can be made available in any form known in the field of cosmetology and dermatology without pharmaceutical restriction other than application to the skin of the face or the body. The compositions according to the invention are advantageously made available in the form of a gel, a cream, an emulsion, a milk, a spray or the like.

These compositions can also contain one or more formulation agents or additives of known and conventional use in cosmetic and dermatological compositions such as (presented as nonlimitative examples): softeners, colorants, film-forming agents, surface-active agents, perfumes, preservatives, emulsifiers, oils, glycols, sebum-absorption agents, vitamins and the like. Those skilled in the cosmetics art know which formulation agents to add to the compositions of the invention and in what quantities in relation to the desired properties.

The cosmetic compositions according to the invention comprise from about 0.1 to about 5%, preferably from about 0.5 to about 2%, of product containing the red algae extract.

EXAMPLE 1

Activity of the Water-alcohol Extract of *Porphyra Umbilicalis* on the Response to Thermal Shock and UV Radiation of Cells in In-vitro Culture For implementation of the experiments described in this example, we used a water-alcohol extract of *Porphyra* (7% alcohol) containing 0.12% of dry matter algae extract. This extract was added at the level of 1% to the culture medium. The final concentration of algae extract was 0.0012%. An alcohol solution of the same concentration (7% alcohol v/v) was used as a control and added at the level of 1% to the culture media (final concentration: 0.07%).

Experiment 1: Demonstration of the Induction of the Synthesis of HSPs by the *Porphyra* Extract The *Porphyra* extract and control solution were added to a culture medium of genetically manipulated CHO (Chinese Hamster Ovary) cells (technologie TSPc®). The cells were then subjected to a thermal shock of 43° C. for 90 minutes. In this model, the synthesis of growth hormone quantitatively determined by an Elisa kit (Boehringer-Roche) reflected the induction of the synthesis of HSP in response to the thermal aggression.

FIG. 1 shows that during the thermal stress the preincubation of the cells with the *Porphyra* extract induced a stimulation of the synthesis of hGH, thus HSP, significantly greater than that observed in the cells not having received the *Porphyra* extract.

Experiment 2: Identification of the HSPs Whose Synthesis is Induced by the *Porphyra* Extract (Thermal Shock and UV)

Specific anti-HSP27, anti-HSP60 and anti-HSP70 antibodies, and the Western blot technique were used. The cells used were HeLa cells for the thermal shock and HaCat cells for the UV stress (0.250 J/cm$^2$ of UV radiation at a wave length of 254 nm).

Figure 2:
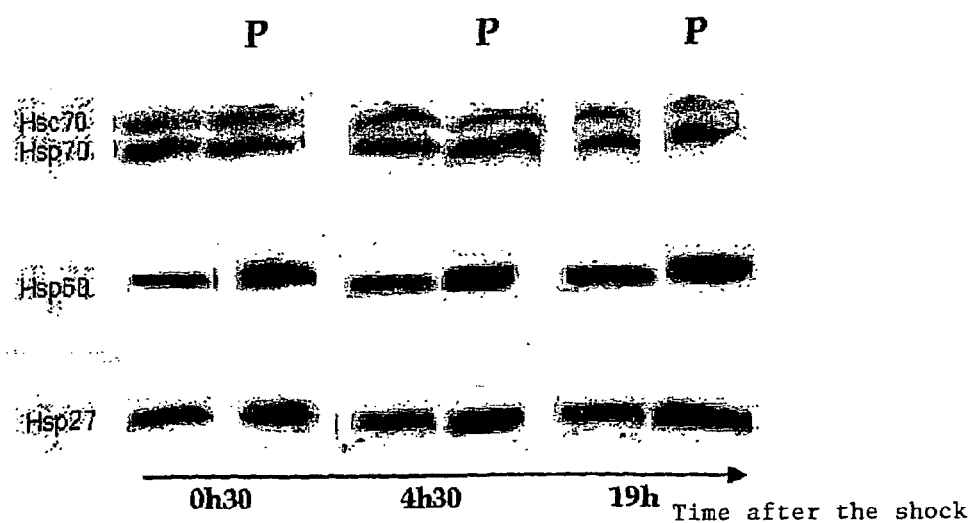
FIG. 2 shows a Western blot analysis of the levels of various HSPs produced by HeLa cells after a thermal shock. The *Porphyra* extract is indicated as E and the control as T.

FIG. 2 shows that the *Porphyra* extract did not modify the production of HSP outside of any aggression, which means that the *Porphyra* extract does not modify the physiological mode of synthesis of the HSPs. In contrast, upon thermal shock, the *Porphyra* extract stimulates the production of proteins HSP60, HSP70 and HSP27. At t=30 minutes, it can be seen that the synthesis of HSP27 and HSP60 was clearly augmented in the cells preincubated with the *Porphyra* extract compared to the control. In contrast, the synthesis of HSP70 was equivalent to that of the control cells. At the times t=4.5 hours and t=19 hours after the thermal shock, the synthesis of HSP27, HSP60 and HSP70 was significantly greater in the cells preincubated with the *Porphyra* extract compared to the control cells.

Figure 3:
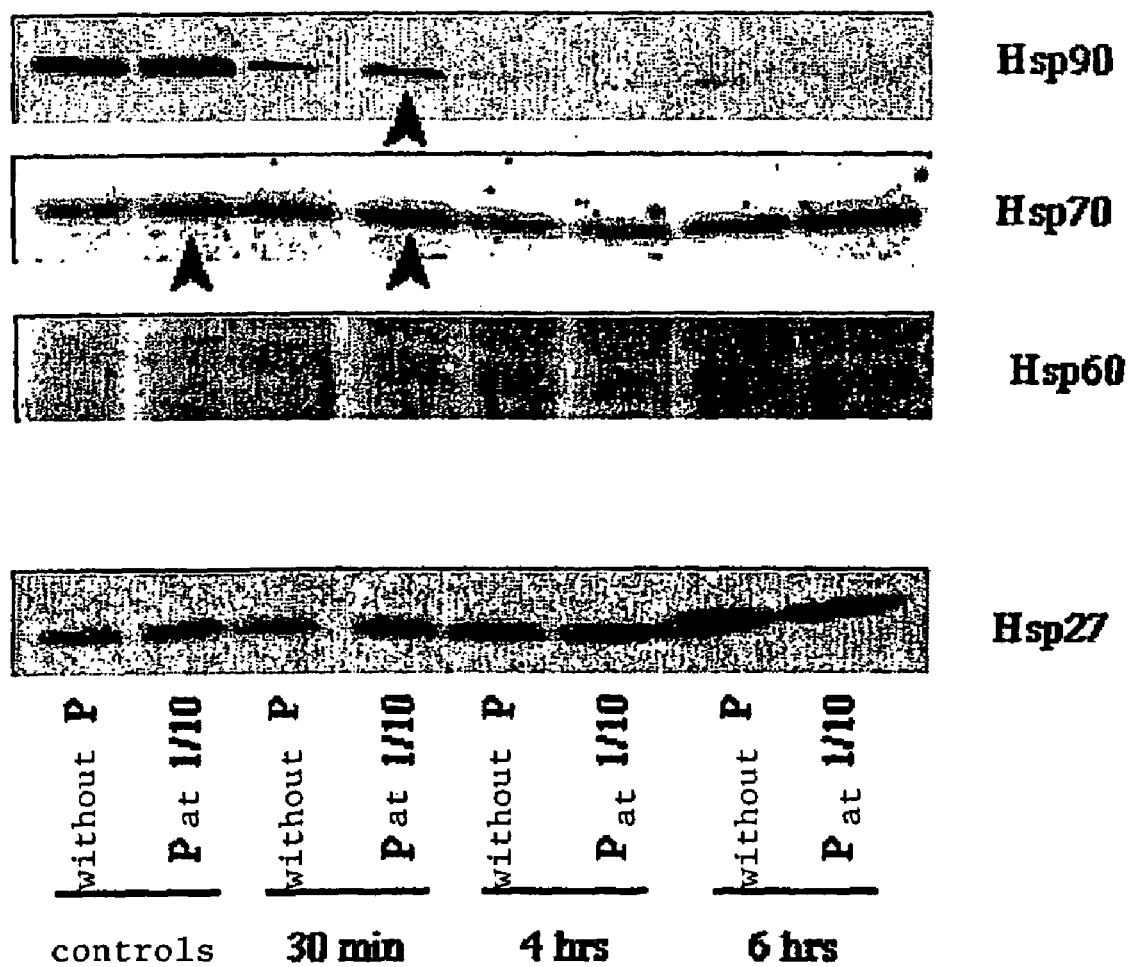
FIG. 3 shows a Western blot analysis of the levels of the different HSPs produced by HaCat cells after UV irradiation. The *Porphyra* extract is indicated as E and the control as T.

FIG. 3 shows that the *Porphyra* extract does not modify the production of HSP outside of any aggression, but rather stimulates the synthesis by the HaCat cells of HSP70 during UV irradiation.

EXAMPLE 2

Formulations of the Water-alcohol Extract of *Porphyra*

1) Nutritional Supplement for Humans

Thirty 700-mg capsules per container. Net weight: 21 g (values rounded).

Ingredients: Extract of *Porphyra* according to the invention in glycerol, virgin borage oil. Capsule (fish gelatin and potato starch). Coating agent: yellow bee's wax.

Vitamins, minerals, plant extracts and lactic ferments can be added.

2) Feed Supplement for Animals

Thirty 700-mg capsules per container. Net weight: 21 g (values rounded).

Ingredients: Extract of *Porphyra* according to the invention in glycerol, virgin borage oil. Capsule (fish gelatin and potato starch). Coating agent: yellow bee's wax.

Vitamins, minerals, plant extracts and lactic ferments can be added.

3) Solar Oral Composition

Forty-five 600-mg capsules (size 6) per container. Net weight: 27 g. Ingredients: Capsule (fish gelatin and potato starch), virgin borage oil. Extract of *Porphyra* according to the invention in glycerol, coating agent: bee's wax, tomato extract, yeast cultured in medium enriched in selenium, vitamin E.

4) Oral Anti-aging Composition for the Skin

Sixty 673-mg capsules per container. Net weight: 40.4 g (rounded values). Ingredients: virgin borage oil, capsule (fish gelatin and potato starch). Dry extract of green tea. Coating agent: bee's wax, extract of *Porphyra* according to the invention in glycerol, hydrolysate of wheat proteins, selenium-enriched yeast, zinc sulfate, manganese sulfate.

| Ingredients | Active principles | Quantity/Unit |
|---|---|---|
| 5) Anti-aging cosmetic composition: antiwrinkle skin care with ceramides | | |
| Hot osmosed water | | 0.4661 kg |
| P O B methyl sodium (Nipagine) | | 0.0020 kg |
| BHT (butyl hydroxy toluene) | | 0.0002 kg |
| P O B pure propyl (Solbrol P) | | 0.0010 kg |
| Cold osmosed water | | 0.0300 kg |
| Triethanolamine 99% (TEA) | | 0.0024 kg |
| DL alpha vitamin E acetate | X (vitamin E) | 0.0050 kg |
| Borage oil (borage cropure) | X | 0.0025 kg |
| Protuline | X (Spiruline) | 0.0 100 kg |
| Preservative para W7 | | 0.0030 kg |
| Perfume base 87 F14892 | | 0.0015 kg |
| Carbopol solution 2% | | 0.1500 kg |
| EDETA BD | | 0.0005 kg |
| Natural glycerin Codex | X (humectant) | 0.0300 kg |
| Monopropylene glycol Codex | | 0.0300 kg |
| Plant ceramide Phytoglycolipid | X | 0.0008 kg |
| Emulgade SE PF (Emulgade SE) | | 0.0700 kg |
| Safacid 16–18 Codex | | 0.0250 kg |
| Sipol C 16 pure | | 0.0100 kg |
| Lanol 14 M | | 0.0050 kg |
| Wheat germ oil | | 0.0250 kg |
| Eutanol G | | 0.0600 kg |
| Cetiol V | | 0.0400 kg |
| Silicone fluid DC 200 350 CS | | 0.0050 kg |
| Uvinul M 40 (Eusolex) | X (UV filters) | 0.0020 kg |
| Escalol 557 | X (UV filters) | 0.0130 kg |
| Porphyra extract | X | 0.0100 kg |
| 6) Cosmetic composition: antipollution multilamellar veil | | |
| Cold osmosed water | | 0.0200 kg |
| Potassium sorbate | | 0.0020 kg |
| P O B pure propyl (Solbrol P) | | 0.0010 kg |
| BHT (butyl hydroxy toluene) | | 0.0001 kg |
| Hot osmosed water | | 0.0967 kg |
| Natrosol 250 HHR | | 0.0035 kg |
| Copper oligoelement | X | 0.0015 kg |
| Zinc oligoelement | X | 0.0015 kg |
| Preservative para W7 | | 0.0030 kg |
| Perfume composition marine F 16184 | | 0.0060 kg |
| Hot osmosed water | | 0.5300 kg |
| Natural glycerin Codex | X (humectant) | 0.0301 kg |
| EDETA BD | | 0.0015 kg |
| P O B pure methyl (Solbrol M) | | 0.0020 kg |
| Triethanolamine 99% (TEA) | | 0.0005 kg |
| Biophilic H | | 0.0401 kg |
| Eutanol G | | 0.0802 kg |

-continued

| Ingredients | Active principles | Quantity/Unit |
|---|---|---|
| Lanol 1688 (Crodamol CAP) | | 0.0701 kg |
| Stabilized sweet almond oil | X | 0.0200 kg |
| Jojoba oil | X | 0.0100 kg |
| Silicone fluid DC 200 350 CS | | 0.0200 kg |
| Silicone DC 345 | | 0.0200 kg |
| Geleol pastilles | | 0.0120 kg |
| Escalol 557 | X (UV filters) | 0.0130 kg |
| Uvinul M 40 (Eusolex) | X (UV filters) | 0.0020 kg |
| DL alpha vitamin E acetate | X (vitamin E) | 0.0030 kg |
| Porphyra extract | X | 0.0100 kg |
| 7) Cosmetic composition: antiwrinkle reparative serum | | |
| Cold osmosed water | | 0.5489 kg |
| P O B methyl sodium (Nipagine) | | 0.0020 kg |
| Lactic acid | | 0.0010 kg |
| Vivid red colorant solution W 3002 A 1/1000 | | 0.0030 kg |
| Natrosol 250 HHR | | 0.00 15 kg |
| Natural glycerin Codex | X (humectant) | 0.0297 k |
| Lubragel MS | X (hydrating agent) | 0.1485 kg |
| Marine elastin | X | 0.0198 kg |
| Tritisol | X (wheat proteins) | 0.0 198 kg |
| Preservative para W7 | | 0.0030 kg |
| Prele hydrumine | X | 0.0030 kg |
| Cold osmosed water | | 0.1683 kg |
| Protuline | X (Spiruline) | 0.0198 kg |
| Kotilen 01 VL (Polysorbate 80) | | 0.0099 kg |
| Perfume composition marine F 16184 | | 0.0020 kg |
| Porphyra extract | X | 0.020 kg |

The invention claimed is:

1. A composition that induces synthesis of stress protective proteins during application of physical or physiological stresses or physiopathological aggressions comprising infections and inflammation on cells, comprising:
   a water-alcohol extract of species *Porphyra umbilicalis* red algae, wherein the extract comprises:
   about 1 to about 5% taurine,
   about 10 to about 25% floridoside,
   one or more of carotenoids and PUFAs,
   one or more water-soluble vitamins, and
   pigments in proportions expressed by weight in relation to the total weight of the extract.

2. The composition according to claim 1, wherein the red algae extract comprises from about 1 to about 30% by weight of the total weight of the composition.

3. The composition according to claim 2, wherein the red algae extract comprises from about 15 to about 25% by weight of the total weight of the product.

4. The composition according to claim 3, further comprising maltodextrins.

5. The composition according to claim 3, further comprising glycerol.

6. The composition according to claim 1, further comprising a preservative agent and which has been subjected to sterilizing filtration.

* * * * *